(12) United States Patent
Gautsch et al.

(10) Patent No.: US 9,459,219 B2
(45) Date of Patent: Oct. 4, 2016

(54) TEMPERATURE CONTROL CHAMBER FOR COMPACT X-RAY MACHINE

(71) Applicant: Anton Paar GmbH, Graz (AT)

(72) Inventors: Josef Gautsch, Graz (AT); Christian Resch, Graz (AT)

(73) Assignee: Anton Paar GmbH, Graz (AT)

( * ) Notice: Subject to any disclaimer, the term of this patent is extended or adjusted under 35 U.S.C. 154(b) by 15 days.

(21) Appl. No.: 14/482,372

(22) Filed: Sep. 10, 2014

(65) Prior Publication Data

US 2015/0071409 A1  Mar. 12, 2015

(30) Foreign Application Priority Data

Sep. 11, 2013 (EP) .................................... 13184017

(51) Int. Cl.
| | | |
|---|---|---|
| G01N 23/20 | (2006.01) | |
| G01N 23/207 | (2006.01) | |
| G01K 7/16 | (2006.01) | |
| F25B 21/04 | (2006.01) | |

(52) U.S. Cl.
   CPC ......... *G01N 23/20033* (2013.01); *F25B 21/04* (2013.01); *G01K 7/16* (2013.01); *G01N 23/20* (2013.01); *G01N 23/207* (2013.01); *G01N 23/20016* (2013.01); *G01N 2223/301* (2013.01)

(58) Field of Classification Search
   CPC ........... G01N 23/20; G01N 23/20025; G01N 23/20033
   USPC .......................................................... 378/80
   See application file for complete search history.

(56) References Cited

U.S. PATENT DOCUMENTS

| | | | | |
|---|---|---|---|---|
| 6,355,217 B1 * | 3/2002 | Kiefersauer | ..... | G01N 23/20025 422/547 |
| 6,881,961 B2 * | 4/2005 | Watanabe | ............ | G01T 1/2928 250/370.15 |

(Continued)

FOREIGN PATENT DOCUMENTS

| | | |
|---|---|---|
| DE | 20109573 U1 | 8/2001 |
| DE | 20 2004 007301 U1 | 8/2004 |

(Continued)

OTHER PUBLICATIONS

Bormann, et al., Determination of Strain Fields in Porous Shape Memory Alloys Using Micro Computed Tomography, Developments in x-Ray Tomography VII, edited by Stuart R. Stock, Proc. of SPIE vol. 7804, 2010 SPIE, 9 pp. <XP 40527846A I>.
Bruker AXS, New Sample Stages for the D8 ADVANCE—Upgrade Your Capabilities, Spec Sheet XRD 34, 2009, Bruker AXS, Karlsruhe, Germany, 2 pp. <XP 55089193A I>.

(Continued)

*Primary Examiner* — Allen C. Ho
(74) *Attorney, Agent, or Firm* — Robert A. Blaha; Smith Tempel Blaha LLC

(57) ABSTRACT

A sample temperature control chamber is described for a benchtop X-ray machine and/or full-protection X-ray machine, which comprises (a) a first chamber part (11) and a second chamber part (12) which can be connected together and are configured so as to form a closed chamber, (b) a sample holder, (c) an integrated temperature control device for controlling the temperature of a sample (P) which is provided on the sample holder, and (d) an active cooling system for dissipating heat from the sample temperature control chamber, the active cooling system comprising a heat sink and/or a fan. A system for X-ray-based analysis of a sample, in particular for X-ray diffraction measurements, is also described.

14 Claims, 3 Drawing Sheets

(56) References Cited

U.S. PATENT DOCUMENTS

| | | | | |
|---|---|---|---|---|
| 6,993,113 | B2* | 1/2006 | Hoshino | G01N 23/201 378/70 |
| 7,135,687 | B2* | 11/2006 | Lacey | A61B 6/4488 250/370.09 |
| 7,281,669 | B2* | 10/2007 | Neuefeind | G01N 23/20025 165/223 |
| 7,400,705 | B2* | 7/2008 | Hoshino | G01N 23/201 378/80 |
| 8,039,812 | B1* | 10/2011 | Crocker | H01L 23/3677 250/370.15 |
| 8,357,894 | B2* | 1/2013 | Toth | G01N 23/20033 250/306 |
| 8,405,040 | B2* | 3/2013 | Luhta | G01T 1/249 250/370.15 |
| 8,581,202 | B2* | 11/2013 | Yamada | G01T 1/248 250/370.09 |
| 8,737,564 | B2* | 5/2014 | McClurg | G01N 23/20008 378/80 |
| 9,022,652 | B2* | 5/2015 | Chupas | G01N 23/20025 378/208 |

FOREIGN PATENT DOCUMENTS

| | | |
|---|---|---|
| DE | 10 2004 029 721 A1 | 1/2005 |
| JP | 03-042561 A | 2/1991 |
| WO | WO 0023795 A1 | 4/2000 |
| WO | 2004005904 A1 | 1/2004 |
| WO | 2013005180 A1 | 1/2013 |

OTHER PUBLICATIONS

Bruker AXS, Non-Ambient Diffraction Solutions—Extract More From Your Sample, Spec Sheet XRD, 2012, Bruker AXS, Karlsruhe, Germany, 12 pp. <XP 55089074A I>.

Bertram, et al., A Compact High Vacuum Heating Chamber for In-Situ X-Ray Scattering Studies, Review of Scientific Instruments 83, 2012, American Institute of Physics., 5 pp. [http:/dx.doi.org/10.1063/1.4746290].

Talaganis, et al., Novel Device for Simultaneous Volumetric and X-Ray Diffraction Measurements on Metal-Hydrogen Systems, Review of Scientific Instruments 80, 2009, American Institute of Physics., 6 pp. [http:/dx.doi.org/10.1063/1.3157086].

* cited by examiner

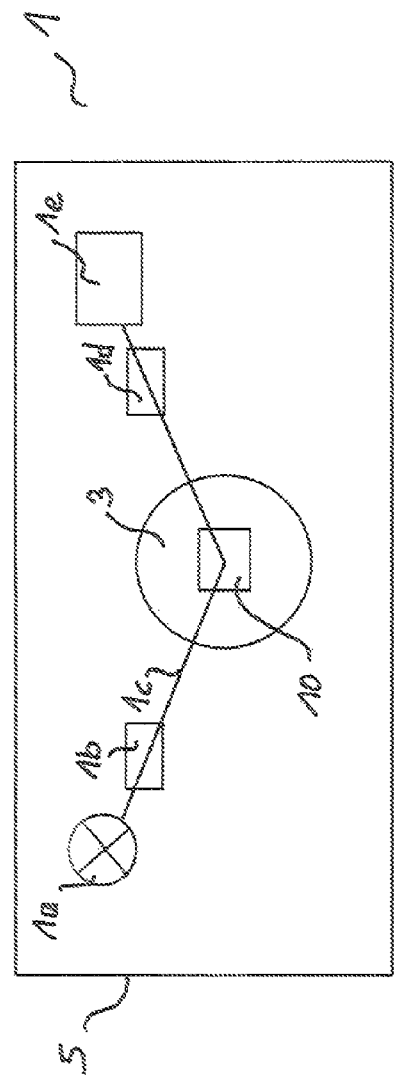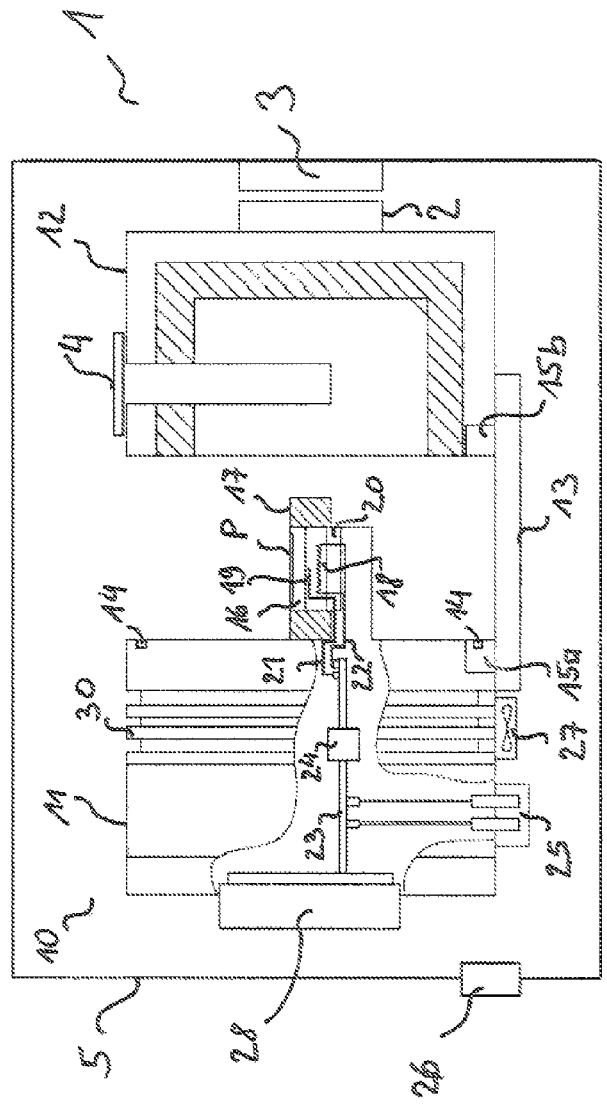
Fig. 1A
Fig. 1B

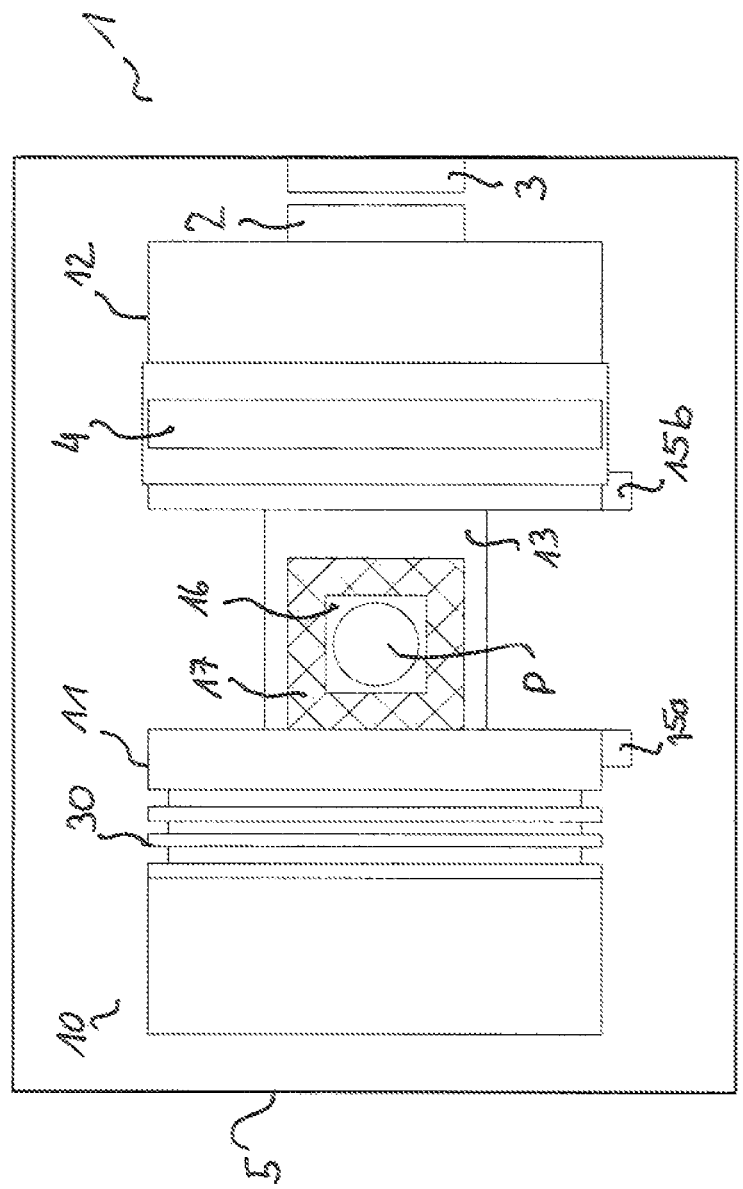

TEMPERATURE CONTROL CHAMBER FOR COMPACT X-RAY MACHINE

CROSS REFERENCE TO RELATED APPLICATION

This application claims the benefit of the filing date of European Patent Application No. 13 184 017.5, filed 11 Sep. 2013, the disclosure of which is hereby incorporated herein by reference.

TECHNICAL FIELD

Embodiments of the invention relate to the field of X-ray-based analysis of materials, in particular to the field of sample temperature control chambers for compact X-ray-based analysis systems.

BACKGROUND

X-ray diffraction experiments are particularly well suited to the structural characterization of homogeneous, inhomogeneous and heterogeneous materials, since the used wavelength of the X-ray beam is of the same order of magnitude as the characteristic spacings in the material to be examined. Experts know that the penetrating X-rays interact elastically with the material and that constructive interference effects can only be observed when the Bragg equation ($n\lambda=2d*\sin(2\theta/2)$) is satisfied under specular conditions (n denotes the integer ordinal number, $\lambda$ the wavelength, $\theta$ the scattering angle, and d denotes the characteristic spacings for the material, for example the lattice planes, or molecular spacings). The experimental results show the characteristic diffraction pattern, which depends on the structure of the material being investigated. The diffraction pattern is used to make predictions as regards the qualitative and quantitative crystal properties of the sample being investigated.

X-ray diffraction (XRD) is a special way of carrying out these material investigations and can be conducted in transmission or reflection geometry. The X-ray beam impinges upon the sample at specific scattering angles $\theta$ which are continuously changed in the experiment (reflection geometry), or the beam is passed through the sample (transmission geometry).

X-ray experiments for elucidating the structure of materials can be carried out either using large facilities such as a synchrotron or linear accelerator, or using so-called laboratory instruments such as standard X-ray diffractometers or small table-top X-ray diffractometers (benchtop X-ray diffractometer). Typical laboratory instruments consist of a radiation source, primary side and secondary side X-ray optics, a sample alignment or adjustment device and a detector unit. Because X-ray tubes are used as the source of radiation, such X-ray laboratory instruments have to be designed as full-protection machines. This means that, for example in Germany, the legally set maximum permissible local dose rate of 3 microsieverts per hour ($\mu$Sv/h) at a distance of 0.1 meters from the completely closed protective housing must not be exceeded (http://www.bfs.de/de/bfs/dienstleitungen/baz/Baz_roev). To operate the X-ray source, existing laboratory X-ray machines require a cooling circuit which usually employs a sealed external fluid circuit, in addition to a specially secured power supply. In order to satisfy the legal requirements for X-ray full-protection devices, it is necessary for these connections to be fed from outside to the X-ray source, depending on the construction of the full-protection machine, via special, secure routes into the machine chamber. In contrast, so-called benchtop X-ray diffractometers are small, compact table-top machines which are usually powered from the standard mains supply, usually do not require an external cooling circuit and thus do not include any external cooling fluid connections. For this reason, benchtop X-ray diffractometers are marketed as simple, transportable full-protection machines which are easy to install, are flexible as regards quality control or can be used as a laboratory instrument for scientific/educational purposes.

Diffraction patterns resulting from the X-ray diffraction experiment vary widely with sample temperature. In the field of material characterization using X-ray diffraction (XRD), investigating the structural properties of materials as a function of temperature has proved to be particularly auspicious, since improved characterization of the material under investigation can be obtained, for example under manufacturing and application conditions. For this reason, a large number of sample temperature control chambers already exist for standard laboratory diffractometers or for synchrotron applications, which are positioned between the X-ray source and the detector. In this respect, the manner of heating and/or cooling the sample in the heating chamber is crucial.

A variety of heatable sample chambers for standard laboratory diffractometers or synchrotron applications are known in the prior art (see, for example, DE 20109573 U1, JPH 0342561 A, DE 102004029721 A1, WO 2013/005180 A1, WO 00/23795 A1, and DE 202004007301 U1). However, these suffer from several disadvantages which render the use of heating chambers of this type in fully protected benchtop X-ray diffractometers impossible. The external cooling circuits of known X-ray heating chambers and their open loop control and closed loop control units and gas flow hook-ups cannot be used in benchtop X-ray diffractometers. The major advantage of the benchtop X-ray diffractometer is that such a sealed, fully protected machine can be used without external cooling circuit connections, without special power supplies and can be readily transported, since they do not require any additional operational and power connections at the location of measurement. The temperature control chambers described in the prior art cannot be used in small benchtop machines, not only because of their geometric dimensions and their weight, but also because they do not comply with the safety requirements for a full-protection machine, since in order to operate the temperature control chambers described in prior art, a variety of external connections are required which are not available in a fully protected machine of table-top dimensions. Particularly problematic in this instance is the feed-through for the coolant.

There may be a need to overcome the disadvantages of the prior art mentioned above and to provide a sample temperature control chamber which can be used with compact benchtop X-ray machines and full-protection X-ray machines in a simple manner and while complying with the safety requirements.

SUMMARY

In accordance with an exemplary first aspect of the invention, a sample temperature control chamber is described for a benchtop X-ray machine and/or full-protection X-ray machine. The described sample temperature control chamber comprises (a) a first chamber part and a second chamber part which can be connected together and are configured so as to form a closed chamber, (b) a sample holder, (c) an integrated temperature control device for controlling the temperature of a sample which is provided on the sample holder, and (d) an active cooling system for dissipating heat from the sample temperature control chamber, the active cooling system comprising a heat sink and/or a fan.

The described sample temperature control chamber is based on the observation that an integrated temperature control device makes it possible to control the temperature of a sample provided on the sample holder without having to provide lines from the sample temperature control chamber leading outside the X-ray analysis machine such as, for example, a benchtop X-ray machine or a full-protection X-ray machine. Inserting the sample temperature control chamber with the sample to be analysed into the X-ray analysis machine means that the analysis can thus be carried out in a simpler and safer manner.

EXEMPLARY EMBODIMENTS

In this document, the term "temperature control" in particular denotes a procedure by means of which the temperature of the sample is adjusted to a value or a series of values.

The first chamber part and the second chamber part are configured such that they can be connected together in order to form a closed chamber. In other words, the sample temperature control chamber is closed by connecting the two chamber parts and is opened by separating the two chamber parts. The sample temperature control chamber preferably has a maximum diameter of 100 mm and a maximum length of 150 mm. In order to analyze a sample, the first chamber part and the second chamber part are separated, the sample is placed on the sample holder and the two chamber parts are connected together so that the sample is located in the chamber which is then closed and isolated from the surrounding atmosphere. The sample temperature control chamber is then introduced into an X-ray analysis machine and fixed, the temperature of the sample is set by the integrated temperature control device for the analysis to be carried out, and the measurements required for the analysis are made. When manipulation or handling of the sample does not require a special protective atmosphere and/or pre-treatment, then if appropriate, the sample can also be changed in the chamber installed in the X-ray analysis machine by opening or separating the two chamber parts and removing the sample carrier.

The active cooling system is configured so as to dissipate heat through one or more chamber walls. To this end, a thermal connection is in particular provided between the sample holder and the chamber wall or chamber walls, for example by means of a metallic connection between the sample holder and the chamber wall. The chamber wall or chamber walls may be formed from aluminum or from a material with similarly good thermal conductivity properties.

The heat sink may comprise a plurality of cooling fins.

The fan may be provided such that it reinforces or assists the dissipation of heat from the heat sink and/or the chamber wall. In particular, the fan may be connected with the control unit in a manner such that the latter can switch the fan on and off. Furthermore, the control unit may be configured such that the rate of rotation of the fan is closed loop controlled, for example as a function of the sample temperature acquired by means of the at least one temperature sensor.

In addition to or as an alternative to the heat sink, a heat exchanger may also be provided.

In accordance with an exemplary embodiment of the invention, the integrated temperature control device comprises a temperature control element for heating the sample up and/or cooling the sample down.

In particular, the temperature control element may be positioned in the vicinity of the sample holder so that heat can be efficiently supplied to or dissipated from the sample.

In accordance with a further exemplary embodiment of the invention, the temperature control element comprises an electrical resistance element for heating the sample up.

In particular, the electrical resistance element may be disposed beneath the sample holder, for example at or in the vicinity of the underside of the sample holder, so that heat can be supplied through the sample holder to the sample when an electric current is fed through the resistance element.

The electrical resistance element makes it possible for the sample temperature to be varied within a range from room temperature to approximately 650° C. or more.

In accordance with a further exemplary embodiment of the invention, the temperature control element comprises a Peltier element for heating the sample up and for cooling the sample down.

The Peltier element may in particular be disposed beneath the sample holder, for example at or in the vicinity of an underside of the sample holder, so that heat can be supplied to or removed from the sample through the sample holder when an electric current flows through the Peltier element, wherein the direction of the electric current determines whether heat is supplied to or removed from the sample.

In embodiments using the Peltier element, active cooling is rendered possible by dissipating the heat arising from cooling the Peltier element so as to obtain sample temperatures below room temperature (ambient temperature). In particular, in such embodiments the sample temperature can move between approximately −20° C. and approximately 200° C., meaning that the thermal coupling to the chamber housing must be as good as possible.

In accordance with a further exemplary embodiment of the invention, the sample temperature control chamber further comprises at least one temperature sensor for acquiring the sample temperature, wherein the temperature control device furthermore comprises a control unit which is connected with the at least one temperature sensor and is configured to control (open loop control or closed loop control) the temperature control element as a function of the sample temperature acquired by the at least one temperature sensor, in order to reach a predetermined sample temperature and/or to apply a temperature profile. By using a plurality of temperature sensors, in particular with samples with poor thermal conductivity, a plurality of sample zones can be characterized simultaneously and be incorporated into the closed loop control or regulation, i.e. the control of the temperature control element.

The at least one temperature sensor may in particular be positioned in the vicinity of the sample holder in order to acquire the sample temperature accurately.

The control unit is connected to the at least one temperature sensor and configured so that the temperature control element is open loop controlled or closed loop controlled such that a predetermined sample temperature is set or such that a predetermined sample temperature range is run through. The control unit may in particular be configured so as to carry out a PID closed loop control algorithm (proportional-integral-differential closed loop control algorithm) or another appropriate closed loop control algorithm.

In accordance with a further exemplary embodiment of the invention, the control unit is provided in the first chamber part, wherein the heat sink and the fan are provided at an outer surface of the first chamber part and wherein the second chamber part comprises a window which is transparent to X-rays.

The control unit may be provided on an internal surface of the first chamber part or on a support fastened inside the first chamber part, and may in particular comprise thermal insulation which serves to protect the electronics contained in the control unit against high temperatures in the sample temperature control chamber.

The sample holder may also be a part of the first chamber part and be provided such that it protrudes relative to the first chamber part in a manner such that, upon connecting the first and second chamber parts, it is accommodated in the second chamber part and is positioned therein such that X-rays penetrating through the window which is transparent to X-rays impinge upon a sample provided on the sample holder. The X-rays reflected and/or transmitted by the sample then also leave the sample temperature control chamber through the window which is transparent to X-rays so that they can be detected by sensors in the X-ray analysis machine.

In other words, the sample holder and the integrated temperature control device may also be part of the first chamber part, wherein the second chamber part essentially defines the volume which forms the closed chamber upon connection of the first chamber part with the second chamber part which is used to investigate the sample in a defined atmosphere using X-rays.

Connection of the two chamber parts may be supported by means of a sliding device which is provided such that the two chamber parts can be slid together and apart.

In accordance with a further exemplary embodiment of the invention, the sample holder may encompass different sample volumes.

In particular, in order to accommodate exchangeable sample pans, the sample holder may be configured in various sizes, wherein the sample pan may also be constructed for various amorphous, crystalline, solid or liquid samples, etc.

In this manner, a wide variety of sample quantities, sizes and types can be accommodated by the sample holder for analysis.

In accordance with a further exemplary embodiment of the invention, the sample temperature control chamber further comprises an input device to enable a predetermined sample temperature or a predetermined sample temperature range to be input by a user.

The input device may in particular be provided on an outer surface of the first chamber part. Furthermore, the input device may, for example, comprise a display and some switches and/or buttons or a keyboard for inputting predetermined temperature values such as, for example, the start temperature and/or end temperature.

In accordance with a further exemplary embodiment of the invention, the sample temperature control chamber further comprises a power connection to connect the sample temperature control chamber with an electrical power supply and/or a data connection to connect the sample temperature control chamber with a data connection of a benchtop X-ray machine and/or full-protection X-ray machine.

The power connection can be used to supply the sample temperature control chamber, in particular the integrated temperature control device, with a power supply for the X-ray analysis machine. This avoids the need for a connection outside the X-ray analysis machine.

In a similar manner, the data connection can be used to connect the sample temperature control chamber, in particular the integrated temperature control device, with a data connection of the X-ray analysis machine. This avoids the need to have an extra line out of the X-ray analysis machine and allows data communication from outside with the integrated temperature control device by means of the data connection which is typically already present in the X-ray analysis machine.

In accordance with a further exemplary embodiment of the invention, the power connection and/or the data connection is/are removable.

Removable connections make manipulation of the sample temperature control chamber outside the X-ray analysis machine easier, for example when preparing samples in a glove box.

In accordance with a further exemplary embodiment of the invention, the sample temperature control chamber further comprises a unit for providing a wireless data connection between the sample temperature control chamber and a benchtop X-ray machine and/or full-protection X-ray machine.

The unit for providing a wireless data connection may in particular comprise a Bluetooth unit (IEEE 802.15.1) or a WLAN unit.

The wireless data connection between the sample temperature control chamber, in particular the control unit for the integrated temperature control device, and the X-ray analysis machine means that manipulation of the sample temperature control chamber is much easier.

In this exemplary embodiment, the unit for providing a wireless data connection may also be used to enable data to be transferred by means of application software to a PC or a mobile device to and/or from the sample temperature control chamber.

In accordance with a further exemplary embodiment of the invention, the sample temperature control chamber further comprises a quick-release element for self-calibrated assembly of the sample temperature control chamber in a benchtop X-ray machine and/or full-protection X-ray machine.

The quick-release element greatly facilitates assembly of the sample temperature control chamber, and above all correct positioning of the sample temperature control chamber in the X-ray analysis machine.

In particular, the quick-release element can be configured so that it can be coupled to a counterpart in an X-ray analysis element.

In accordance with a further exemplary embodiment of the invention, the sample temperature control chamber further comprises means for sealing the closed chamber in a gas-tight manner.

The means for sealing in a gas-tight manner enables, inter alia, transport of the sample temperature control chamber into and out of a glove box without affecting the atmosphere in the sealed chamber.

In accordance with a second aspect of the invention, a system is described for X-ray-based analysis of a sample, in particular for X-ray diffraction measurement. The system described comprises (a) a benchtop X-ray machine or a full-protection X-ray machine and (b) a sample temperature control chamber in accordance with the first aspect or in accordance with one of the above embodiments, which is configured for introduction and assembly in the benchtop X-ray machine or full-protection X-ray machine.

Essentially, the basis of the system described is the same as the sample temperature control chamber in accordance with the first aspect or one of the embodiments described above, namely that a temperature control device integrated into the sample temperature control chamber allows the temperature of a sample provided on the sample holder to be controlled without having to provide lines from the sample temperature control chamber out of the X-ray analysis machine, such as a benchtop X-ray machine or a full-protection X-ray machine, for example. Thus, the system allows an X-ray-based analysis to be carried out in a simpler and safer manner.

In summary, a sample temperature control chamber is provided which consists of two separate parts wherein one part consists of the integrated temperature control device, optionally with an active cooling unit, and the second part consists of the sample chamber itself. Thus, the use of an external regulator or an external cooling system is not necessary for the sample temperature control chamber for a benchtop X-ray diffractometer or similar analytical instrument.

Embodiments of the invention offer a light, compact variation of a temperature control chamber for an X-ray analysis machine, ensures easy manipulation and handling, and requires a single, easily made electrical contact line for a full-protection machine. The temperature control chamber is preferably provided with a quick-release element with a counterpart on the machine and thus can be easily installed and dismantled and calibrated. In accordance with embodiments of the invention, it can be configured such that no additional calibration is required.

Moreover, the temperature control chamber can provide for gas-tight sealing of the chamber. Because of its geometric dimensions and the gas-tight sealing of the chamber, it can easily be placed in the fast antechamber of a glove box, where samples can be prepared under inert conditions. Thus, it can be ensured that the material to be investigated cannot come into direct contact with personnel or air and/or sensitive samples can be manipulated solely in a protective atmosphere.

Furthermore, the temperature control chamber may comprise exchangeable sample pans for various amorphous, crystalline, solid or liquid samples. The temperature control chamber can then be placed again in the benchtop X-ray diffractometer without disturbing the set sample atmosphere. In this manner, no additional gas lines are required for this temperature control chamber.

Advantageously, the accuracy as regards the temperature is better than 0.5° C., depending on which heating element is used in the respective embodiment and how the active cooling system is regulated or closed loop controlled. The chamber does not require expensive and unwanted flow-through cooling, for example using a coolant gas or coolant liquid.

BRIEF DESCRIPTION OF THE DRAWINGS

FIG. 1A shows a diagrammatic side view of a system for X-ray-based analysis with an X-ray machine or a benchtop X-ray diffractometer and a sample temperature control chamber in accordance with one embodiment.

FIG. 1B shows a side view of a sample temperature control chamber in the open state in accordance with one embodiment.

FIG. 3 shows a top view of a sample temperature control chamber in the open state in accordance with an embodiment.

DETAILED DESCRIPTION

Figure 1C:
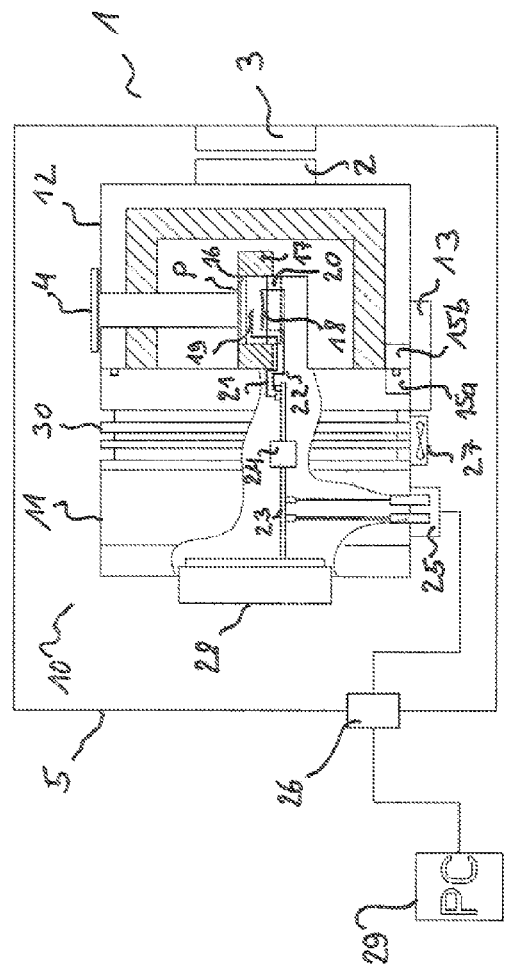
FIG. 1C shows a side view of the sample temperature control chamber shown in FIG. 1B in the closed state.

The diagrammatic side view of FIG. 1A shows an embodiment of a system for X-ray-based analysis. The system comprises an X-ray machine or a benchtop X-ray diffractometer 1 with an X-ray source 1a, primary side optics 1b, X-ray beam 1c, a goniometer 3, secondary side optics 1d, a detector 1e and a specially constructed housing 5, which prevents inadmissibly high radiation outside the X-ray machine or benchtop X-ray diffractometer 1. The system further comprises a sample temperature control chamber 10 which is also known as an X-ray heating chamber 10 and is mounted on the goniometer 3.

FIG. 1B shows a side view of a sample temperature control chamber 10 in the open state in accordance with an embodiment. The sample temperature control chamber 10 is provided for use with an X-ray analysis machine such as the benchtop X-ray diffractometer 1 which is shown.

The side view in FIG. 1B shows the sample temperature control chamber 10, which in general consists of a first part 11 (closed loop control and supply part) and a second part 12 (sample chamber part). The sample P to be analyzed is introduced horizontally into the sample chamber part 12 by means of a sliding device 13 upon closing the sample temperature control chamber 10. The entire sample temperature control chamber 10 can be mounted by means of the quick-release element 2 on the goniometer 3 of the benchtop X-ray diffractometer 1. The two chamber parts 11, 12 are connected together in a gas-tight manner by means of a sealing member 14 and are closed by means of a lock 15a, 15b. The sealing member 14 and the lock 15a, 15b are configured such that the entire sample temperature control chamber 10 or X-ray heating chamber can easily be slid in both directions into an antechamber of a glove box without breaking the atmosphere subsisting inside the sample temperature control chamber 10.

FIG. 1C shows a side view of the sample temperature control chamber 10 shown in FIG. 1B in the closed state. During the measuring procedure, the X-rays used for the measurement can penetrate the closed sample temperature control chamber 10 via the window 4 in the sample temperature control chamber 10 which is transparent to X-rays and can interact with the sample P. The window 4 preferably consists of polymer compounds or is formed from beryllium, and thus is matched to the geometry of the sample temperature control chamber 10 so that the scattered X-rays leave the sample temperature control chamber 10 through the same window 4 and can strike an X-ray detector (not shown). Alternatively, two windows 4 may also be used.

The sample P is in a sample carrier 16 which is positioned on the sample table 17. In accordance with embodiments of the invention, the sample carrier 16 can be individually exchangeable in order to be capable of analyzing different samples such as powder samples, liquids etc. The temperature control element 18 in the form of an electrical resistance element and a temperature sensor 19 to detect the sample temperature is located directly in the sample table 17. The sample table 17 is internally thermally insulated from the housing 5 of the sample temperature control chamber 10 by means of an insulation unit 20, in order to avoid unwanted direct heating of the housing 5. The temperature control element 18 and temperature sensor 19 are connected with the control unit 23 via measuring cables 21, 22. It also accommodates the electrical supply 24 for the sample temperature control chamber 10.

In accordance with embodiments of the invention, the control unit 23 and electrical supply 24 are preferably only connected, via a common contact 25, with the full-protection connection 26 at the housing 5 of the benchtop X-ray diffractometer 1 (see FIG. 1C). This means that a closed loop control is possible via an external control unit (not shown) or via the control and evaluation unit (personal computer) 29 integrated into the benchtop X-ray diffractometer 1. Alternatively, it is possible to pre-set the chamber temperature via a control panel 28 directly on the sample temperature control chamber 10.

Directly integrated into the closed loop control and supply part 11 is the active cooling unit of the sample temperature control chamber 10. Preferably, this consists of cooling fins 30 or other heat sinks with as large a surface as possible in combination with one or more fans 27 which transport heat away by forced convection.

Figure 2:
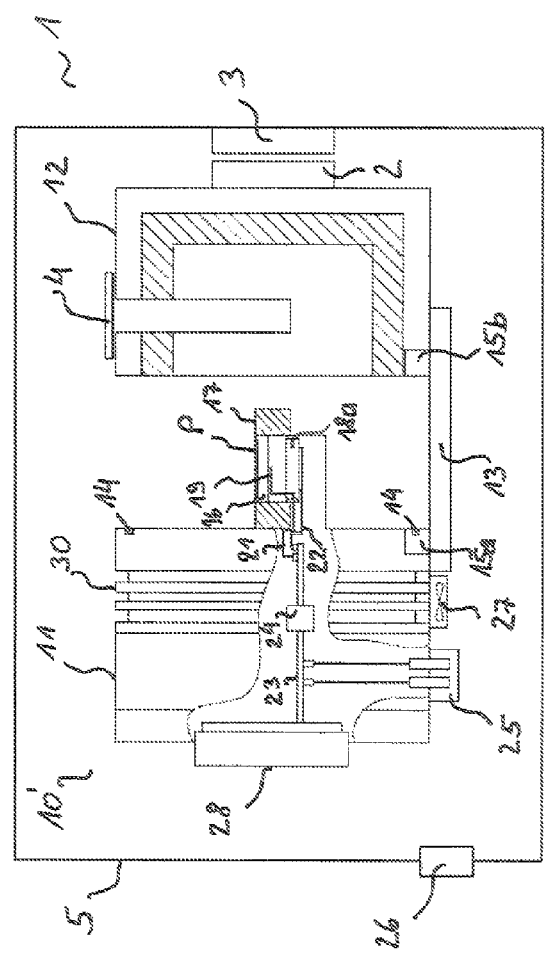
FIG. 2 shows a side view of a sample temperature control chamber in the open state in accordance with a further embodiment.

FIG. 2 shows a side view of a sample temperature control chamber 10' in the open state in accordance with a further embodiment. The sample temperature control chamber 10' is substantially identical to the sample temperature control chamber 10 shown in FIGS. 1B and 1C. Consequently, repetition of any descriptions of identical elements will be dispensed with. The essential difference between this and the sample temperature control chamber 10 described above is that the sample temperature control chamber 10' uses a Peltier element 18a as the temperature control element. Here, the heat conduction between the housing of the sample temperature control chamber 10' and the sample table 17 must be as good as possible. Using active internal cooling, it is now possible to conduct the heat arising from the cold side of the Peltier element away and to use it, in quasi-combination with the fan 27, as active counter-cooling. In this manner, in this embodiment, a temperature range of −20° C. to 200° C. can be obtained, which is a substantial improvement over the prior art. DE 202004007301 U1, in comparison, mentions temperature ranges from 0° C.-100° C. The Peltier element 18a can also be used for rapid cooling of the sample P in the sample holder by reversing the polarity, whereupon the now warmer back of the Peltier element is cooled by the forced cooling or the heat arising is conducted away.

FIG. 3 shows a top view of a sample temperature control chamber in the open state in accordance with one of the embodiments described above. FIG. 3 shows the top view of the open sample temperature control chamber 10, 10' which, as described above, consists of the first part 11 and the second part 12, with the lateral locking device 15a, 15b. FIG. 3 also shows the quick-release element 2, the goniometer 3 and the benchtop X-ray diffractometer 1. It can also be seen that the window 4 which is transparent to X-rays is preferably formed as one piece. When the sample temperature control chamber is open, it is possible to remove the sample P or the sample carrier 16 from the sample temperature control chamber 10 from above or from the side.

The invention claimed is:

1. A sample temperature control chamber for at least one of a benchtop X-ray machine and a full-protection X-ray machine, the sample temperature control chamber comprising:
   a first chamber part and a second chamber part configured to form a closed chamber;
   an integrated temperature control device for controlling a temperature of a sample provided on a sample holder, the integrated temperature control device comprising a temperature control element;
   at least one temperature sensor for acquiring a sample temperature;
   a control unit connected to the at least one temperature sensor and configured to control the temperature control element as a function of the sample temperature to obtain at least one of reaching a predetermined sample temperature and applying a temperature profile; and
   an active cooling system for dissipating heat, wherein the active cooling system comprises at least one of a heat sink and a fan,
   wherein the control unit is provided in the first chamber part, wherein the heat sink and the fan are provided at an outer surface of the first chamber part and wherein the second chamber part comprises a window which is transparent to X-rays.

2. The sample temperature control chamber as claimed in claim 1, wherein the sample holder is constructed to accommodate at least one of amorphous, crystalline, solid and liquid samples.

3. The sample temperature control chamber as claimed in claim 1, wherein the temperature control element comprises an electrical resistance element for heating the sample up.

4. The sample temperature control chamber as claimed in claim 1, wherein the temperature control element comprises a Peltier element for heating the sample up and for cooling the sample down.

5. The sample temperature control chamber as claimed in 1, further comprising:
   a sliding device connected to one of the first chamber part and the second chamber part.

6. The sample temperature control chamber as claimed in claim 1, wherein the control unit and an electrical supply are connected via a common contact to an external control unit.

7. The sample temperature control chamber as claimed in claim 1, wherein the sample holder may encompass different sample volumes.

8. The sample temperature control chamber as claimed in claim 1, further comprising an input device for enabling at least one of a predetermined sample temperature and a predetermined sample temperature range to be input by a user.

9. The sample temperature control chamber as claimed in claim 1, further comprising at least one of a power connection to an electrical power supply and a data connection to at least one of a benchtop X-ray machine and a full-protection X-ray machine.

10. The sample temperature control chamber as claimed in claim 9, wherein at least one of the power connection and the data connection is removable.

11. The sample temperature control chamber as claimed in claim 1, further comprising:
    a unit for providing a wireless data connection to at least one of a benchtop X-ray machine and a full-protection X-ray machine.

12. The sample temperature control chamber as claimed in claim 1, further comprising a quick-release element for self-calibrated assembly in at least one of a benchtop X-ray machine and a full-protection X-ray machine.

13. The sample temperature control chamber as claimed in claim 1, further comprising:
    means for sealing the closed chamber in a gas-tight manner.

14. A system for X-ray-based analysis of a sample, the system comprising:

one of a benchtop X-ray machine and a full-protection X-ray machine; and a sample temperature control chamber, configured for introduction and assembly in the one of the benchtop X-ray machine and the full-protection X-ray machine, the sample temperature control chamber comprising a first chamber part and a second chamber part which can be connected together and configured to form:

a closed chamber;

a sample holder;

an integrated temperature control device for controlling a temperature of a sample provided on the sample holder, the integrated temperature control device including a temperature control element;

at least one temperature sensor for acquiring a sample temperature;

a control unit connected to the at least one temperature sensor and configured to control the temperature control element as a function of the sample temperature to obtain at least one of reaching a predetermined sample temperature and applying a temperature profile; and an active cooling system for dissipating heat from the closed chamber, wherein the active cooling system comprises at least one of a heat sink and a fan, wherein the control unit is arranged in the first chamber part, the heat sink and the fan are arranged along a surface of the first chamber part and the second chamber part includes a window transparent to X-rays.

* * * * *